US010682396B2

(12) United States Patent
Kost et al.

(10) Patent No.: US 10,682,396 B2
(45) Date of Patent: Jun. 16, 2020

(54) CONTROLLED RELEASE SYSTEM FOR PULMONARY DELIVERY OF SURFACTANT PROTEIN D

(71) Applicants: B. G. NEGEV TECHNOLOGIES AND APPLICATIONS LTD, Beer Sheva (IL); CHILDREN'S HOSPITAL MEDICAL CENTER, Cincinnati, OH (US)

(72) Inventors: Joseph Kost, Omer (IL); Tamar Traitel, Beer Sheva (IL); Riki Goldbart, Lehavim (IL); Shani Attias, Kiryat Motzkin (IL); Paul Scot Kingma, Cincinnati, OH (US); Jeffrey A. Whitsett, Cincinnati, OH (US); Giora Enden, Tel-Aviv (IL)

(73) Assignees: B.G. NEGEV TECHNOLOGIES AND APPLICATIONS LTD, Beer Sheva (IL); CHILDREN'S HOSPITAL MEDICAL CENTER, Cincinnati, OH (US)

( * ) Notice: Subject to any disclaimer, the term of this patent is extended or adjusted under 35 U.S.C. 154(b) by 0 days.

(21) Appl. No.: 15/735,005

(22) PCT Filed: Jun. 9, 2016

(86) PCT No.: PCT/IL2016/050606
§ 371 (c)(1),
(2) Date: Dec. 8, 2017

(87) PCT Pub. No.: WO2016/199146
PCT Pub. Date: Dec. 15, 2016

(65) Prior Publication Data
US 2018/0161404 A1  Jun. 14, 2018

Related U.S. Application Data

(60) Provisional application No. 62/172,881, filed on Jun. 9, 2015.

(51) Int. Cl.
*A61K 38/17* (2006.01)
*A61K 9/51* (2006.01)
*A61K 9/14* (2006.01)
*A61K 9/00* (2006.01)
*A61P 11/00* (2006.01)

(52) U.S. Cl.
CPC .......... *A61K 38/395* (2013.01); *A61K 9/0073* (2013.01); *A61K 9/146* (2013.01); *A61K 9/5153* (2013.01); *A61K 38/1709* (2013.01); *A61P 11/00* (2018.01); *A61K 9/0019* (2013.01); *A61K 9/0043* (2013.01)

(58) Field of Classification Search
None
See application file for complete search history.

(56) References Cited

U.S. PATENT DOCUMENTS

| 4,962,091 A | 10/1990 | Eppstein et al. | |
|---|---|---|---|
| 2002/0130430 A1* | 9/2002 | Castor | A61K 9/1694 264/14 |
| 2007/0293449 A1* | 12/2007 | Cui | A61K 9/1272 514/44 A |
| 2008/0242615 A1* | 10/2008 | Ikegami | A61K 38/395 514/1.5 |
| 2011/0189104 A1 | 8/2011 | Whitsatt et al. | |

FOREIGN PATENT DOCUMENTS

| WO | WO 90/11768 | 10/1990 |
|---|---|---|
| WO | WO 00/23569 | 4/2000 |
| WO | WO 02/17878 | 3/2002 |
| WO | WO 2007/056195 | 5/2007 |

OTHER PUBLICATIONS

Hidalgo, A. et al. Barrier or Carrier? Pulmonary surfactant and drug delivery. European Journal of Pharmaceutics and Biopharmaceutics. Feb. 20, 2015. (vol. 95) pp. 117-127.
International Search Report and Written Opinion received in PCT Application No. PCT/IL2016/050606, dated Aug. 7, 2016.
Ungaro, F. et al. Engineered PLGA nano- and micro-carriers for pulmonary delivery: challenges and promises. Dec. 31, 2012. Journal of Pharmacy and Pharmacology (vol. 64, No. 9) pp. 1217-1235.
Raghavendran, K. et al. Surfactant Therapy of ALI and ARDS. Jul. 1, 2011. Crit Care Clin. (vol. 27, No. 3) pp. 525-559.
Crouch et al; "Molecular Structure of Pulmonary Surfactant Protein D (SP-D)" The Journal of Biological Chemistry vol. 269, No. 25, pp. 17311-17319. (1994).
Persson et al; "Surfactant Protein D Is a Divalent Cation-dependent Carbohydrate-binding Protein" The Journal of Biological Chemistry vol. 265, No. 10, pp. 5755-5760. (1990).
Zhang et al; "Activity of Pulmonary Surfactant Protein-D (SP-D) in Vivo Is Dependent on Oligomeric Structure" The Journal of Biological Chemistry vol. 276, No. 22, pp. 19214-19219. (2001).

* cited by examiner

*Primary Examiner* — Jeffrey T. Palenik
(74) *Attorney, Agent, or Firm* — Knobbe, Martens, Olson & Bear, LLP

(57) ABSTRACT

A controlled release system includes surfactant protein D (SPD) and a carrier suitable for controlled release that can be polylactic-co-glycolic acid (PLGA). The system can be in the form of a nanoparticle. A pharmaceutical composition includes the system and a pharmaceutically acceptable carrier. Methods of treatment of a disease, disorder or condition associated with a decreased level of SPD in a subject, or for pulmonary delivery of SPD, include administering the pharmaceutical composition to a subject in need of such treatment.

10 Claims, 6 Drawing Sheets

CONTROLLED RELEASE SYSTEM FOR PULMONARY DELIVERY OF SURFACTANT PROTEIN D

FIELD OF THE INVENTION

The present invention relates to a controlled release system for administration of surfactant protein D for treating lung disease.

BACKGROUND OF THE INVENTION

Preterm infants, particularly those of very low birth weight that were born between week 23 and week 28 of gestation, suffer from a very high incidence of respiratory distress syndrome (RDS) related to pulmonary immaturity and inability to make pulmonary surfactant lipids and proteins. These infants are supported by the use of oxygen, ventilators, and routine administration of surfactant replacement. The surfactant replacement preparations currently at use contain surfactant protein (SP) B and SPC but do not contain SPA, SPD, or other innate host-defense proteins (Ikegami et al. 2006; WO 90/11768). SPD is a hydrophilic surfactant protein that decreases pulmonary inflammation and facilitates normal surfactant lipid structure and recycling. Its use as a surfactant replacement has been described (Ikegami et al. 2006; WO 07/056195; WO 02/17878; WO 00/023569; US 2011/0189104; U.S. Pat. No. 7,266,403) but never implemented commercially, possibly due to problems associated with consistent delivery of large oligomerised proteins such as SPD. Furthermore, since repeated intubation or instillation into the airway is challenging in small infants, a sustained release vehicle that provides surfactant replacement, including SPD, for long periods of time in lungs of preterm infants would be highly desirable, but there is currently no system or device for sustained release of SPD in the alveoli of infants or adults.

SUMMARY OF THE INVENTION

According to one aspect, the present invention provides a controlled release system comprising surfactant protein D (SPD) and a carrier suitable for controlled release.

According to another aspect, the present invention provides a nanoparticle comprising SPD and PLGA.

According to an additional aspect, the present invention provides a pharmaceutical composition comprising the controlled release system or nanoparticle according to the invention.

According to yet another aspect, the present invention provides a method of treatment of a disease, disorder or condition associated with a decreased level of SPD in a subject, comprising administering the system or nanoparticle according to the invention or a pharmaceutical composition thereof to said subject.

According to still another aspect, the present invention provides a method for pulmonary delivery of SPD comprising administering to a subject in need thereof the system or nanoparticle according to the invention or a pharmaceutical composition thereof.

DETAILED DESCRIPTION OF THE INVENTION

Figure 1A:
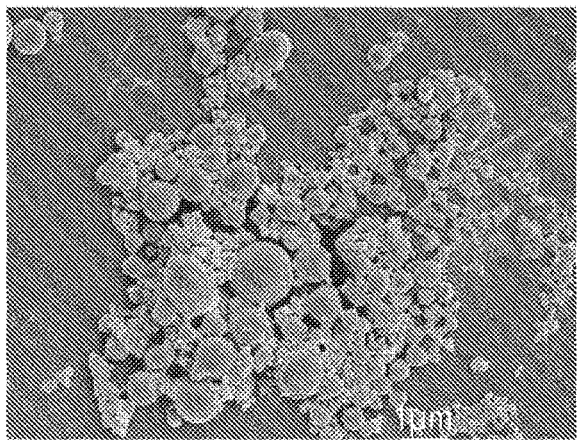
FIGS. 1A-1D show scanning Electron Microscopy (SEM) images of poly lactic-co-glycolic acid (PLGA) nanoparticles (NPs) with surfactant protein D (SPD). A and B: PLGA 1A NPs with SPD; C and D: PLGA 7A NPs with SPD. A and C: at ×10,000 magnification and B and D: at ×35,000 magnification.
Figure 1B:
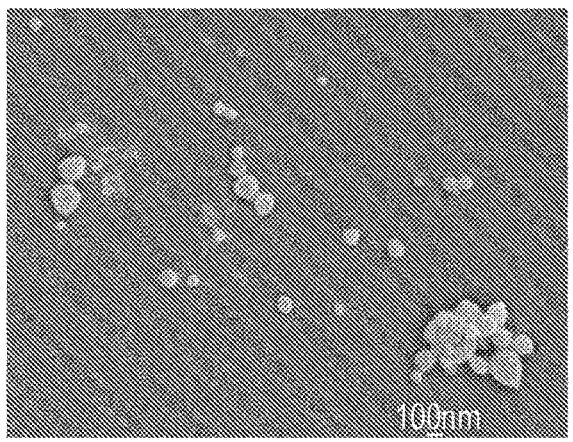
Figure 1C:
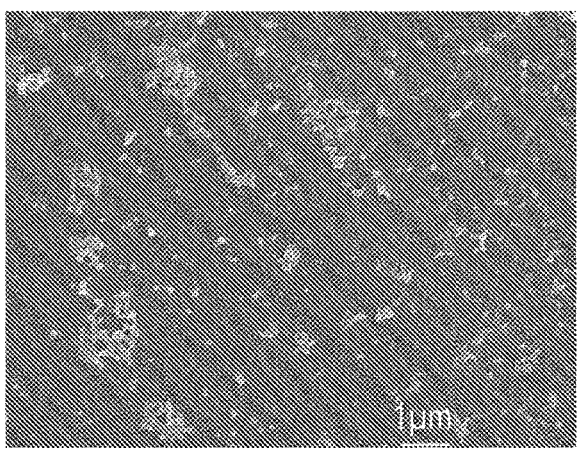
Figure 1D:
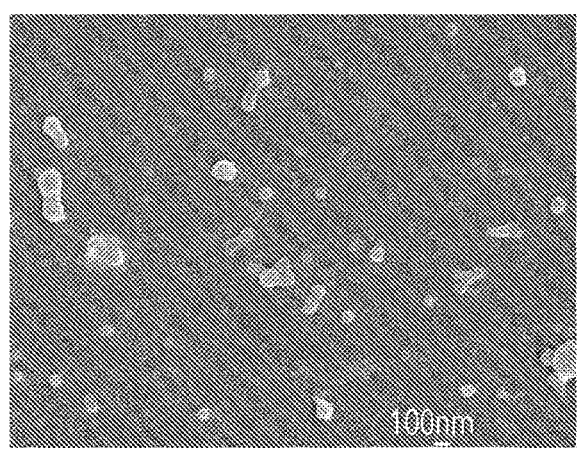

In the present application, the inventors have found that poly lactic-co-glycolic acid (PLGA) can form nanoparticles with surfactant protein D (SPD). Importantly, it was found that the SPD protein is released from the nanoparticles and maintains its biological activity, and therefore a system comprising PLGA and SPD can be used as a carrier in a delivery system for controlled release of SPD in the lungs.

Poly(lactic-co-glycolic acid) (PLGA) is a biodegradable and biocompatible FDA-approved copolymer used as a vehicle for delivery, including controlled delivery of drugs.

PLGA is synthesized by means of ring-opening co-polymerization of two different monomers, the cyclic dimers (1,4-dioxane-2,5-diones) of glycolic acid and lactic acid. Polymers can be synthesized as either random or block copolymers thereby imparting additional polymer properties. During polymerization, successive monomeric units (of glycolic or lactic acid) are linked together in PLGA by ester linkages, thus yielding linear, aliphatic polyester as a product. Depending on the ratio of lactide to glycolide used for the polymerization, different forms of PLGA can be obtained: these are usually identified in regard to the molar ratio of the monomers used (e.g. PLGA 75:25 identifies a copolymer whose composition is 75% lactic acid and 25% glycolic acid).

Additional carriers may be used in accordance with the present invention instead of PLGA, including polymeric carriers such as polylactic acid (PLA), polyglycolic acid (PGA), chitosan, gelatin, polycaprolactone and poly-alkyl-cyanoacrylates (Kumari et al, 2010). In some embodiments the carrier is biodegradable.

Examples 1-3 show that PLGA and SPD form complexes having the size of nanoparticles. Example 5 further demonstrates that SPD protein continues to be released from these nanoparticles for a duration of at least a week, and Example 6 shows that the released SPD is biologically active. Examples 9 and 10 show that SPD is released from the SPD NPs of the invention after administration to lungs of wild-type or knock-out mice.

Accordingly, the present invention provides a controlled release system comprising SPD and a carrier suitable for controlled release.

According to some embodiments, the carrier of the system/nanoparticle is polymeric, i.e. comprising a polymer. In some embodiments the carrier is PLGA.

The term "complex" as used herein refers to a molecular entity formed by loose association involving two or more component molecular entities (ionic or uncharged), or the corresponding chemical species; and this term and the term "system" are used herein interchangeably.

The ratio of lactic acid to glycolic acid in the PLGA polymer of the system/nanoparticle may vary. The ratio which was used in the experiments of the present invention is 50:50. However, other ratios may also be suitable as indicated below. Accordingly, in some embodiments, the ratio of lactic acid to glycolic acid in said PLGA is 50:50, 65:35, 70:30, 75:25, 82:18 or 85:15, in particular the ratio is 50:50.

The polymer may be at any of various inherent viscosities between 0.05 and 7.0 dL/g, for example 0.05 to 1 dl/g or between 0.1 to 0.7 dl/g (depending on the molecular weight, molecular weight distribution, and consistency of the polymer). The molecular weight of the PLGA may be selected from between 1 to 200, between 3 to 150 or between 5 to 100 kDa. In the examples presented hereinbelow, two types of PLGA polymers were used, with molecular weights of 96 kDa and (inherent viscosity of 0.63 dl/g) and 5.6 kDa (and inherent viscosity of 0.11 dl/g).

From Example 2 it can be seen that the radius of the nanoparticles is about 100 nm. Accordingly, in some embodiments, the system is a nanoparticle or a microparticle, in particular a nanoparticle. In some embodiments, the average radius of said nanoparticle is selected from between 20 and 300, between 50 and 150 nm, or about 100 nm.

The zeta potential affects the tendency of the particles to aggregate; charged particles have a lesser tendency to aggregate due to the repulsing forces of particles having the same charge, while neutrally charged particles have a tendency to aggregate. There is therefore an advantage to particles having a charge. The SPD-loaded PLGA nanoparticles disclosed in herein have a negative zeta potential of about −35 mV (Example 3).

In some embodiments the present invention provides a nanoparticle comprising SPD and PLGA.

SPD was prepared as previously described (Ikegami et al., 2006). In some embodiments, the SPD may be recombinant SPD. In some embodiments, the SPD is a mammalian SPD, in particular human SPD.

In some embodiments, the system does not contain surfactant components other than SPD. For example, the system comprises SPD but is void of SPA, SPB or SPC.

The system/nanoparticle of the present invention is prepared by standard methods used in the art such as the double emulsion evaporation technique, emulsification-solvent evaporation technique, or the nanoprecipitation method also called the interfacial deposition method (Danhier et al, 2012).

The term "controlled release" is used herein interchangeably with the terms "prolonged-action", "repeat-action", "extended release", and "sustained-release" and refers to the release of an active agent at predetermined intervals or gradually, in such a manner as to make the contained active agent available over an extended period of time.

In some embodiments, the system of the invention as described hereinabove is for use in pulmonary delivery of SPD, i.e. for use in delivery of SPD to the lungs.

The present invention also provides a pharmaceutical composition comprising the system/complex/nanoparticle of the invention as described hereinabove and a pharmaceutically acceptable carrier.

Methodology and components for formulation of pharmaceutical compositions are well known and can be found, for example, in Remington's Pharmaceutical Sciences, Eighteenth Edition, A. R. Gennaro, Ed., Mack Publishing Co. Easton Pa., 1990. Pharmaceutical compositions for use in accordance with the present invention thus may be formulated in conventional manner using one or more physiologically acceptable carriers comprising excipients and auxiliaries, which facilitate processing of the active agents into preparations that can be used pharmaceutically. Proper formulation is dependent upon the route of administration chosen.

The pharmaceutical composition may be aerosolized by any known method such as by a pneumatic, jet or ultrasonic nebulizer. Methods and devices for aerosolization are described, for example, in Labiris and Dolovich 2003, *Br. J. Clin. Pharmacol.* 56: 600-612, and in Ibrahim et al., 2015, *Medical Devices: Evidence and Research* 8: 131-139.

In some embodiments, the pharmaceutical composition is in the form of an aerosol, spray or mist.

The term "pharmaceutically acceptable carrier" refers to a vehicle which delivers the active components to the intended target and which will not cause harm to humans or other recipient organisms. As used herein, "pharmaceutical" will be understood to encompass both human and veterinary pharmaceuticals. Useful carriers include, for example, water, acetone, ethanol, ethylene glycol, propylene glycol, butane-1,3-diol, isopropyl myristate, isopropyl palmitate, mineral oil and polymers composed of chemical substances like polyglycolic acid or polyhydroxybutyrate or natural polymers like collagen, fibrin or polysaccharides like chitosan and alginate. The carrier may be in any form appropriate to the mode of delivery, for example, solutions, colloidal dispersions, emulsions (oil-in-water or water-in-oil), suspensions, gels, sprays and the like.

Several human lung diseases are characterized by decreased levels of bronchoalveolar SPD and may therefore be treated by administration of the system of the present invention.

The term "decreased levels of bronchoalveolar SPD" as used herein refers to partial or complete deficiency of bronchoalveolar SPD as compared with the level of bronchoalveolar SPD in normal healthy individual(s). It has been shown for several diseases, including acute respiratory distress syndrome (ARDS) and respiratory syncytial virus (RSV) that the levels of SPD, even if they are within the normal range, correlate with mortality rates or with disease outcome. Accordingly, the term "decreased levels of bronchoalveolar SPD" may be also used to further refer to a decreased level of bronchoalveolar SPD which is still within the normal range but is associated with poor prognosis of a disease.

Non-limiting examples of individuals having decreased levels of bronchoalveolar SPD, i.e. individuals in need for treatment, include preterm infants, particularly those of very low birth weight that were born between about week 23 and about week 28 of gestation, and individuals with a mutated spd gene resulting in reduced expression or altered activity.

Thus, in some embodiments, the system/nanoparticle or the pharmaceutical composition of the invention as described hereinabove is for use in the treatment of a disease, disorder or condition associated with a decreased level of a SPD.

In some embodiments, the disease, disorder or condition is selected from chronic obstructive lung disease (COPD), asthma, acute bronchitis, chronic bronchitis, bronchopulmonary dysplasia, emphysema, infant respiratory distress syndrome (IRDS), acute respiratory distress syndrome (ARDS), lung infections, persistent pulmonary hypertension, lung hypoplasia, cancer, cystic fibrosis, alveolar proteinosis, upper respiratory inflammation, congenital SP-B deficiency, respiratory syncytial virus (RSV), allergic rhinitis, and/or influenza. In some embodiments, the disease, disorder or condition is selected from IRDS, cystic fibrosis, and emphysema.

The present invention further provides a method of treatment of a disease, disorder or condition associated with a decreased level of SPD in a person, comprising administering to said person a therapeutically effective amount of the system of the invention as described hereinabove or a pharmaceutical composition thereof.

The present invention also provides a method for pulmonary delivery of SPD comprising administering to a subject in need thereof a therapeutically effective amount of the system of the invention as described hereinabove or a pharmaceutical composition thereof.

As explained above, the controlled release feature of the system allows for a lower frequency of administration thereby causing less inconvenience to the patient.

The term "treating" or "treatment" as used herein includes alleviating, abrogating, substantially inhibiting, slowing, reducing or reversing the progression of a condition, substantially ameliorating or reducing clinical symptoms of a condition, substantially preventing the appearance of clinical symptoms of a condition, or complete cure of the disease.

The controlled release system/nanoparticle of the invention or the pharmaceutical composition comprising it can be administered by various pulmonary delivery methods, for example, by inhalation, nebulization, intratracheal administration such as by intratracheal injection, or a nasal spray.

Pharmaceutical compositions suitable for use in context of the present invention include compositions wherein the active ingredients are contained in an amount effective to achieve the intended purpose. More specifically, a "therapeutically effective amount" means an amount of an active ingredient effective to prevent, alleviate or ameliorate symptoms of a disease or disorder or prolong the survival of the subject being treated.

Determination of a therapeutically effective amount is well within the capability of those skilled in the art, especially in light of the detailed disclosure provided herein.

Depending on the severity and responsiveness of the condition to be treated, dosing can be of a single or a plurality of administrations or a single administration of a slow release composition, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

The term "about" as used herein means that values of 10% or less above or below the indicated values are also included.

The invention will now be illustrated in the following non-limiting examples.

EXAMPLES

Materials and Methods

Materials

50:50 poly lactic-co-glycolic acid (PLGA) 7A, MW 96 kDa with an inherent viscosity of 0.63 dl/g and 50:50 PLGA 1A, MW 5.6 kDa with an inherent viscosity of 0.11 dl/g were purchased from Lakeshore Biomaterials. Polyvinyl alcohol (PVA, MW 85-124 kDa; 87-89% hydrolyzed, 9002-89-5), Ethyl acetate (34848) and Sodium Hydroxide (1310-73-2) were obtained from Sigma-Aldrich Inc. Surfactant protein D (SPD) protein was synthesized in Cincinnati Children's Hospital Medical Center (CCHC) by methods as described in Ikegami et al. 2006. Micro BCA™ protein assay (23235) was purchased from ORNAT, Biochemicals & Laboratory Equipment Ltd. Thiazolyl Blue Tetra-zolium Bromide (MTT) (M2128) was purchased from Sigma-Aldrich Inc. Hydrochloric acid 32% (08460201), was purchased from Bio-Lab. DMEM high glucose medium (01-055-1A), Fetal Bovine Serum (FBS) (04-121-1A), Trypsin Ethylene diamine tetra acetic acid (EDTA) (03-052-1B), L-glutamine (03-020-1B), Penicillin-streptomycin (03-031-1B) were purchased from Biological Industries Beit Haemek.

Fabrication of Nanoparticles

Two types of PLGA 50:50 with different molecular weights (PLGA 7A-96 kDa and PLGA 1A-5.6 kDa) were used to prepare PLGA nanoparticles (NPs) using a double emulsion evaporation technique (w/o/w=water/oil/water). 100 mg PLGA were dissolved in 2 ml of ethyl acetate solvent in a glass tube. 2.5 mg of surfactant protein D (SPD) were dissolved in 100 μL DDW and then added to the polymer/solvent mixture and emulsified by sonication (Q-Sonica, 700 W, 20 KHz, 35% amplitude) for 10 s in an ice bath to form a primary emulsion. The solution was then added at a high setting vortex to 4 ml of an external aqueous phase, containing 5% w/v PVA (polyvinyl alcohol) as a stabilizer. The contents were sonicated 3 times for 10 s (35% amplitude). The resulting solution was then added drop wise into 50 ml of a 0.5% w/v aqueous PVA solution under magnetic stirring. The resulting nano-sized particles were stirred in solution for 3 h to allow for ethyl acetate evaporation. The NPs were centrifuged, washed 3 times with DDW, and finally resuspended in 4 ml DDW and dried in a lyophilizer.

Dynamic Light Scattering (DLS)

Mean particle size and size distribution of the SPD-loaded and empty PLGA 1A and 7A NPs were determined by dynamic light scattering using CGS-3 (ALV, Langen, Germany). The laser power was 20 mW at the He—Ne laser line (632.8 nm). Correlograms were calculated by ALV/LSE 5003 correlator, which were collected at 90°, during 10 s, 20 times, at 25° C. The samples were diluted to an appropriate concentration using phosphate-buffered saline (PBS) (PH=7.4). The PBS was previously filtered through a 0.22 am membrane filter (Millipore, USA) to avoid the presence of any interfering particles. All measurements were carried out in triplicates; hence, each value is the mean of three independent readings within a batch and an error represents the standard deviation of the mean particle size as an index of particle size polydispersity.

Scanning Electron Microscopy

The surface morphology and shape of the nanoparticles were investigated by scanning electron microscopy (HRSEM, JSM-7400F). To this end, approximately one drop of nanoparticles suspension was mounted on an aluminum stub and sputter coated for 30 s with a thin layer of gold under vacuum and then observed with a scanning electron microscope operating at 3 kV and 20° C.

Zeta Potential

The surface charge of the NPs was determined by Zeta potential. Samples from DLS were transferred to U-tube cuvette (DTS1060C, Malvern) for subsequent zeta potential measurements using Zetasizer (ZN-NanoSizer, Malvern, England). SPD-loaded and empty PLGA 1A and 7A NPs were measured at automatic mode, at 25° C., and the Smoluchowski model was used to calculate the zeta potential. For each sample the zeta potential value was presented as the average value of three runs.

In Vivo Toxicity Test

To determine if treatment with nanoparticles induces a chronic inflammatory response by looking primarily at macrophage and neutrophils in Bronchiolar Lavage Fluid (BALF), mice were treated with either 10 μg/g body weight (n=10), 20 μg/g body weight PLGA nanoparticles (n=4), or PBS for controls (n=5). 2 and 4 weeks after tracheal injection subsets of mice were lavaged and some had lungs inflation fixed for histology. BALF was spun at 4000×g for 10 minutes and pelleted cells resuspended in 150 ul PBS. 140 ul of suspension was used for Cytospin, 5 minutes at 500 RPM. Slides were allowed to dry and H&E stain was performed and cells were counted.

SPD Nanoparticle Elution Profile 7.5 mg of SPD-loaded NPs were mixed with 150 ul PBS, spun for 5 minutes at 800 RPM to wash. Wash process was repeated and fresh PBS placed on bead after second wash. Tubes containing particles were rotated at room temp and samples were collected daily for 1 week, stored at −20° C. and analyzed by silver stain gel according to standard procedures.

Bacterial Aggregation Assay

The biological activity of SPD released from NPs was analyzed using Bacterial Aggregation Assay (Hartshorn et al. 1998, Am. J. Physiol.—Lung Cellular and Molecular Physiology 274(6):L958-L969). *E. coli* Y1088 cultures were spun down, media removed, and washed in 1×TBS (Tris-buffered saline). Bacteria was spun down again and resuspended in Hank's Balanced Salt Solution (HBSS) such that the absorbance reading at A700 is 1. Samples are loaded into Beckman DU 640 spectrophotometer cuvette containing 5 mM $CaCl_2$, *E. coli*, and SPD (5 ul of eluate per elution day tested) and A700 readings are taken every 2.5 minutes using a kinetics program. Control sample with PBS was also run for comparison.

MTT Assay

MTT stock solution was prepared by dissolving 5 mg of MTT powder in 1 mL of filter sterilized PBS. The cell medium was replaced with 0.5 mL of fresh starvation medium and 50 μL of MTT solution was added to each well. Cells were incubated for 4 hours in the incubator after which 1 mL of MTT solvent, dimethylsulfoxide (DMSO), was added to each well. The cell plates were incubated over night at room temperature in a sterile hood. Absorbance of each well was read at wavelength of 570 nm and reference of blank solution (MTT+DMEM medium+DMSO) was used. Cell viability was calculated by equation 1:

$$\text{Cell viability (\%)} = \frac{\text{Optical density } (OD) \text{ of the treated cells}}{OD \text{ of the non-treated cells}} \times 100\% \quad (1)$$

SP-D ELISA

In Human Surfactant Protein D ELISA, standards and samples were incubated in microplate wells pre-coated with monoclonal anti-human surfactant protein D antibody. 100 μl of standard and sample were added to the microplate wells and incubate for 2 hour at room temperature on an orbital shaker at 300 rpm. After incubation, the wells were washed 5 times. 100 μl of Biotin labelled monoclonal anti-human SP-D antibody was added into each well and incubated with the captured SP-D for 60 minutes on an orbital shaker at 300 rpm. After another washing (5 times), 100 μl of Streptavidin-HRP Conjugate was added and shaken for 60 minutes. After incubation and the last washing step, the remaining HRP conjugate is allowed to react with 100 μl Substrate Solution (TMB) that was added to each well. The microplate was incubated for 15 min after covering the plate with aluminum foil. The reaction was stopped by addition of 100 μl acidic solution and absorbance of the resulting yellow product was measured at 450 nm wavelength. The absorbance is proportional to the concentration of surfactant protein D.

Example 1: Scanning Election Microscope

In order to investigate the physicochemical characterization of nanoparticles prepared by the double emulsion method, nanoparticles were observed by Scanning Electron Microscope. As shown in FIGS. 1A-1D, the SPD-loaded PLGA NPs were spherical and had a smooth surface without pores or cavities which could affect the release of the encapsulated protein. The PLGA 1A NP size was not homogeneous compared to PLGA 7A NPs. In both types of PLGA there was no difference in shape between the NPs with protein and the empty NPs.

Example 2: Dynamic Light Scattering (DLS)

Figure 2:
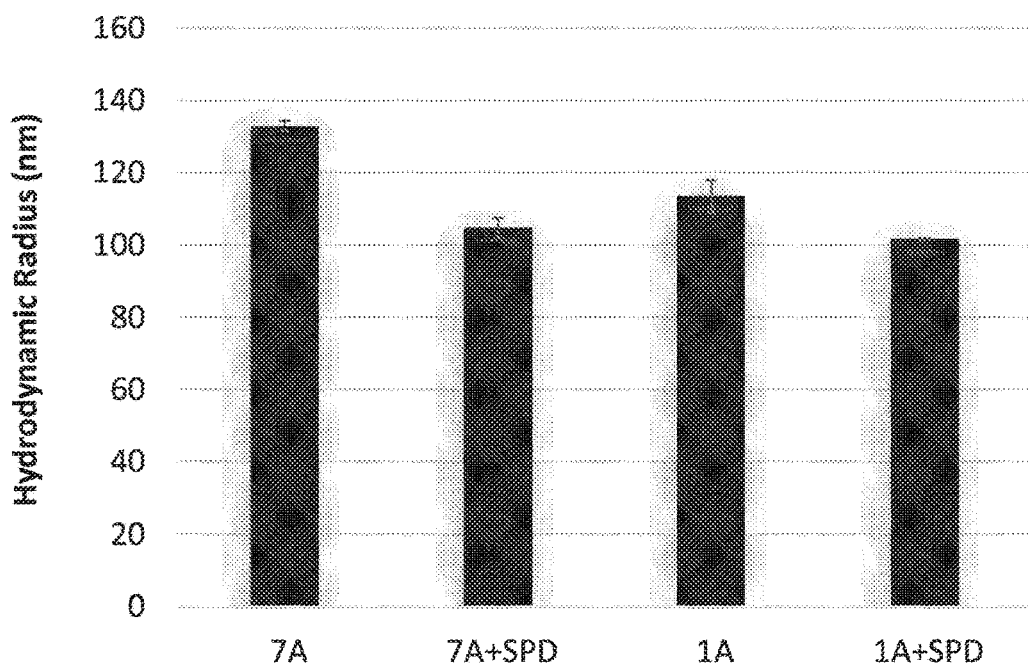
FIG. 2 shows hydrodynamic radius of PLGA NPs with SPD in PBS solution measured with Dynamic Light Scattering (DLS). From left to right: PLGA-7A, PLGA-7A with SPD, PLGA-1A, PLGA-1A with SPD.
Figure 3:
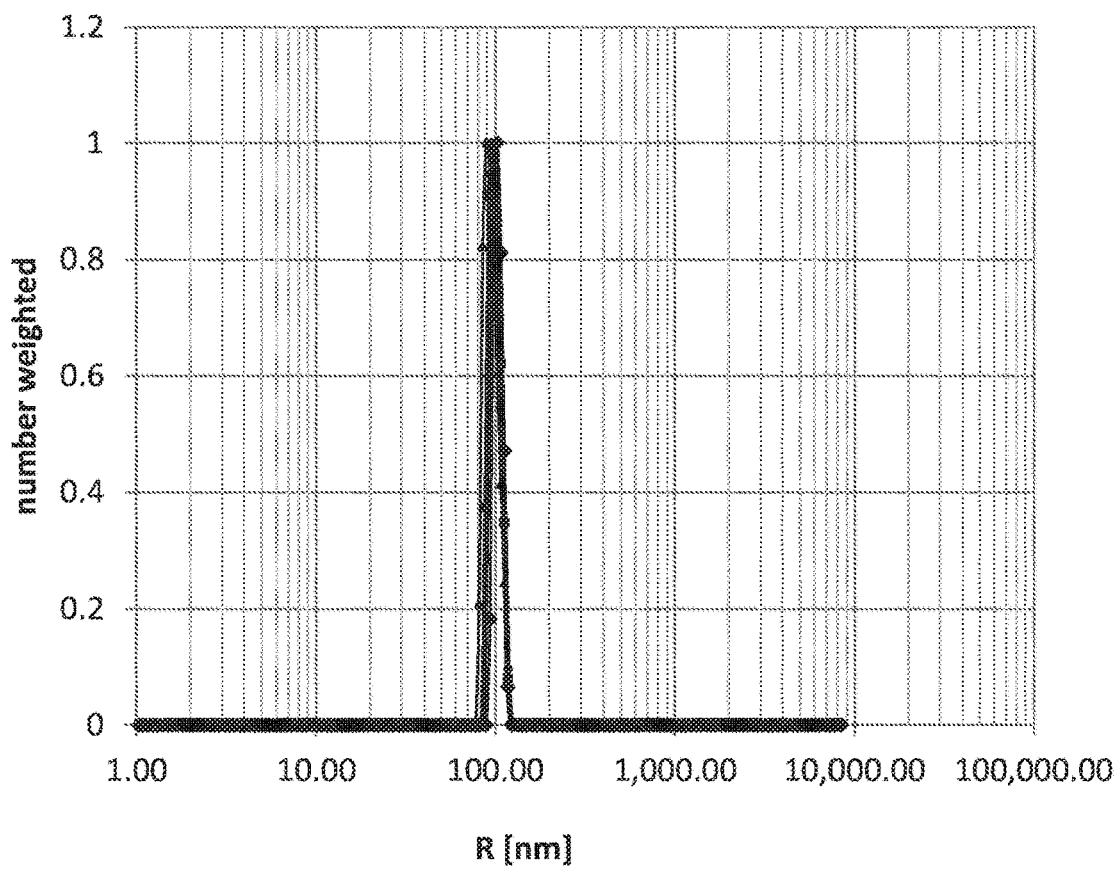
FIG. 3 shows size distribution of PLGA 7A NPs with SPD measured with Dynamic Light Scattering (DLS) (n=3).

The DLS method was used in order to determine the mean size and size distribution of the NPs. DLS can calculate the hydrodynamic diameter of a particle from Stokes-Einstein equation by measuring the scattered light of the particles that are moving in Brownian motion. PLGA-NPs 1A and 7A had similar average hydrodynamic radius of approximately 100 nm with or without protein (FIG. 2). The size distribution of nanoparticles is shown in FIG. 3. PLGA 1A with SPD showed two populations of particles on DLS and the SEM results. One population demonstrated particles with hydrodynamic radius of around 100 nm, similar to empty NPs, and an additional population with radius of around 600 nm. For further experiments or treatment the population including the larger particles was removed by filtration before using the NPs.

Example 3: Zeta Potential

Figure 4:
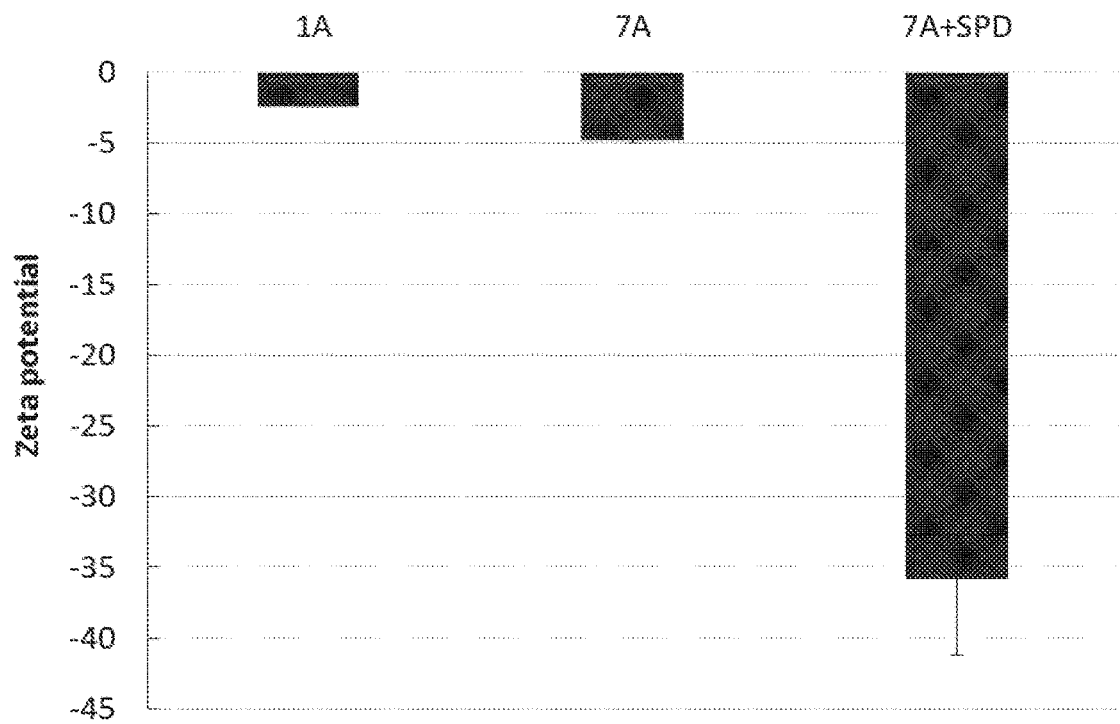
FIG. 4 shows Zeta potential of PLGA 1A and 7A NPs with and without SPD in PBS solution. From left to right: PLGA 1A, PLGA 7A, PLGA 7A with SPD.

Zeta potential measures the surface charge of particles and can give indication of the tendency of the particle suspension to aggregate and sediment. FIG. 4 shows the Zeta potential of PLGA 1A without SPD and PLGA 7A with and without SPD. The low values indicate that the charge of the empty NPs is 0 and the particles aggregate as can be observed from the SEM images.

NPs including SPD showed a highly negative Zeta potential (−35 mV). The pI value of SPD is 5-8 according to the literature. The large value of the zeta potential is predictive of high colloidal stability.

Example 4: In Vivo Toxicity Text

Figure 5:
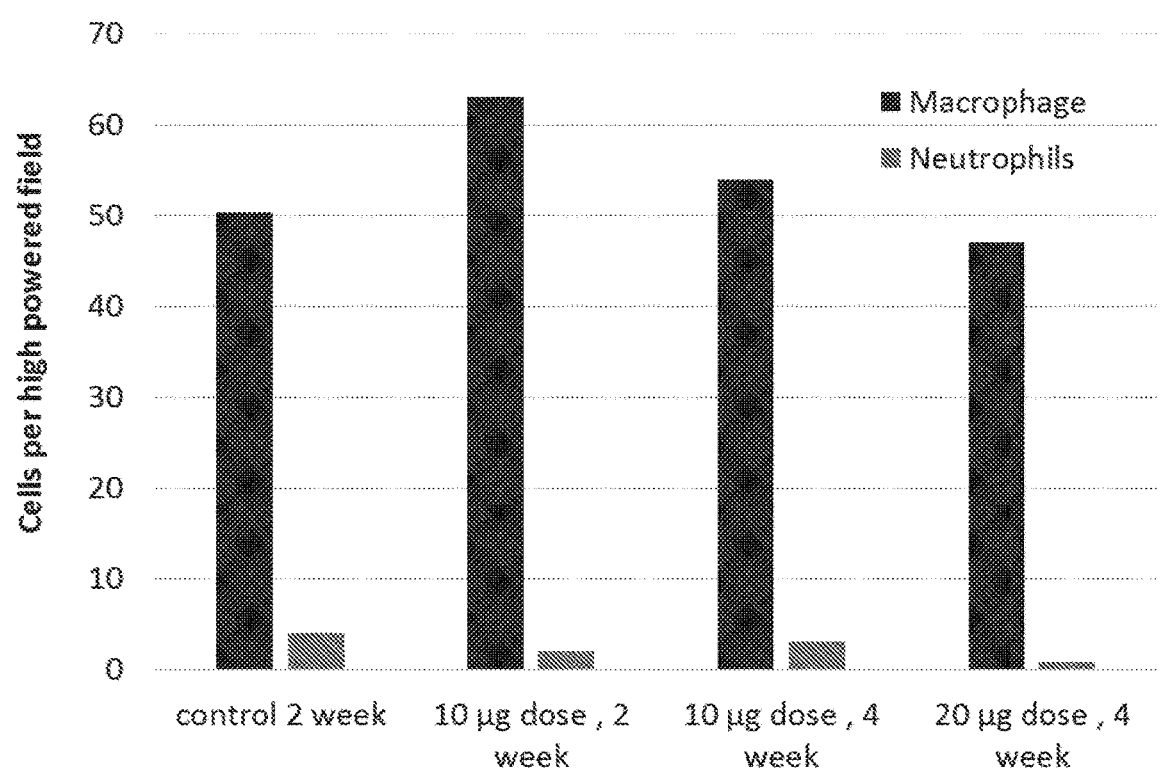
FIG. 5 shows toxicity test of C57bl/6 mice by intra-tracheal injection of PLGA 7A empty NPs at 10 and 20 µg particles per gram body weight, 2 or 4 weeks after the injection. Control group was injected with 100 µl sterile PBS and tested after 2 weeks. Each group: Macrophages: (left black bars), neutrophils: (right gray bars).

FIG. 5 presents a toxicity test of C57bl/6 mice intratracheal injection with PLGA 7A NPs at 10 or 20 μg particles per gram of body weight. The control group is a solution with 100 μl sterile PBS. In this test the number of macrophage and neutrophils recovered was compared to the control group and tested after 2 and 4 weeks.

As we can see in FIG. 5, the number of macrophage and neutrophils was similar to the number in the control group indicating that the PLGA NPs were not toxic to the mice.

Example 5: Surfactant Protein D (SPD) Nanoparticle Elution Profile

Figure 6:
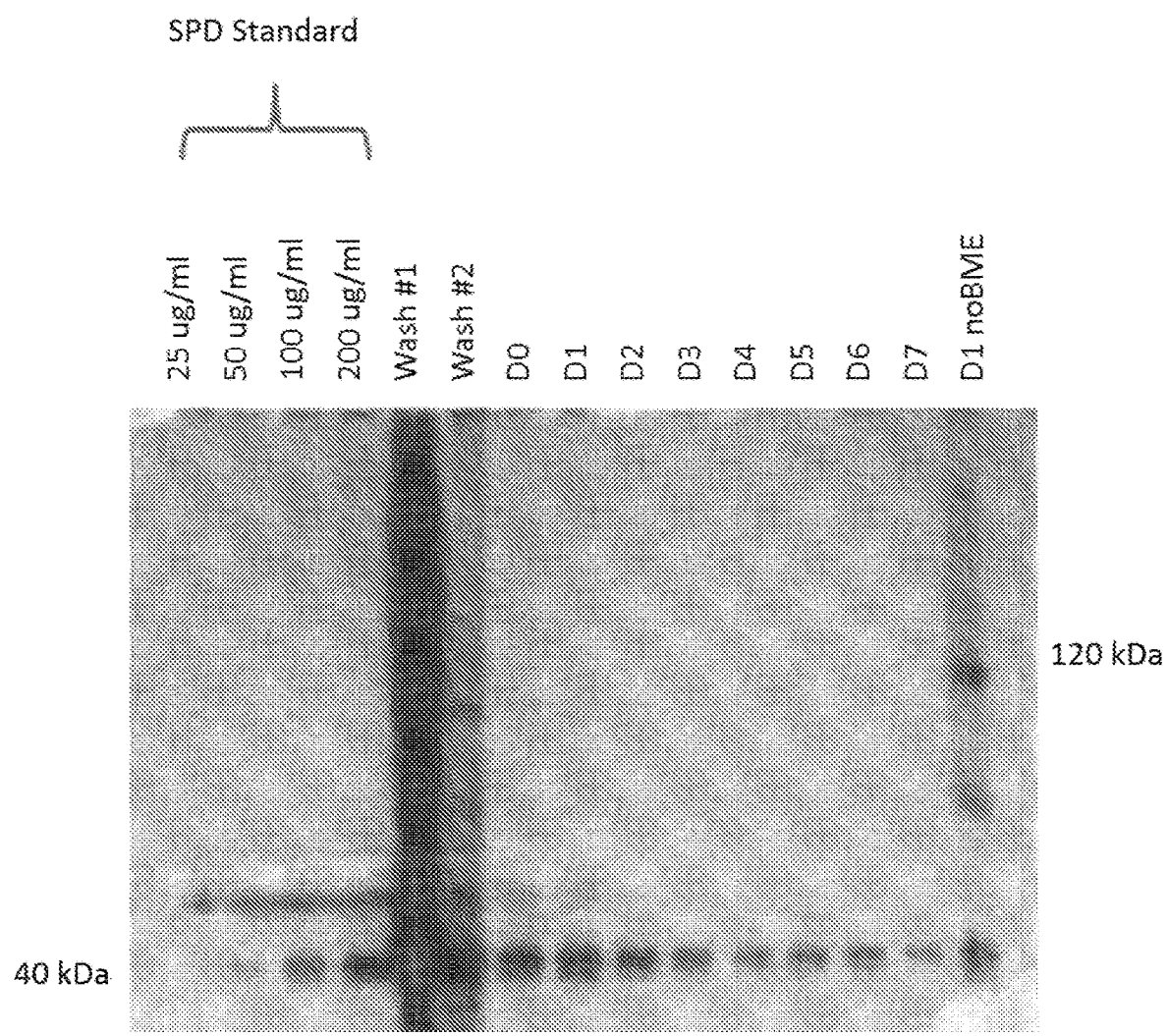
FIG. 6 shows SDS-PAGE analysis of SPD released from NPs during one week. First four lanes from the left include different concentrations of SPD (left to right: 25, 50, 100 and 200 µg/ml), next two lanes include washes, and the following lanes include daily samples from day 0 to day 7. The right-most lane is sample taken at day 1 without β-ME (normally added to each sample to keep a denatured state). 40 kD marks the approximate location of the SPD monomer (43 kDa), and 120 kD marks the approximate location of the SPD trimer (129 kDa).

Samples of surfactant protein-D (SPD) that were released from PLGA NPs during one week were analyzed every day using silver stain gel. As we can see in FIG. 6, SPD keeps being released from nanoparticles for a duration of at least one week and the integrity of the protein was also maintained during the encapsulation process.

Example 6: Bacterial Aggregation Assay

Figure 7:
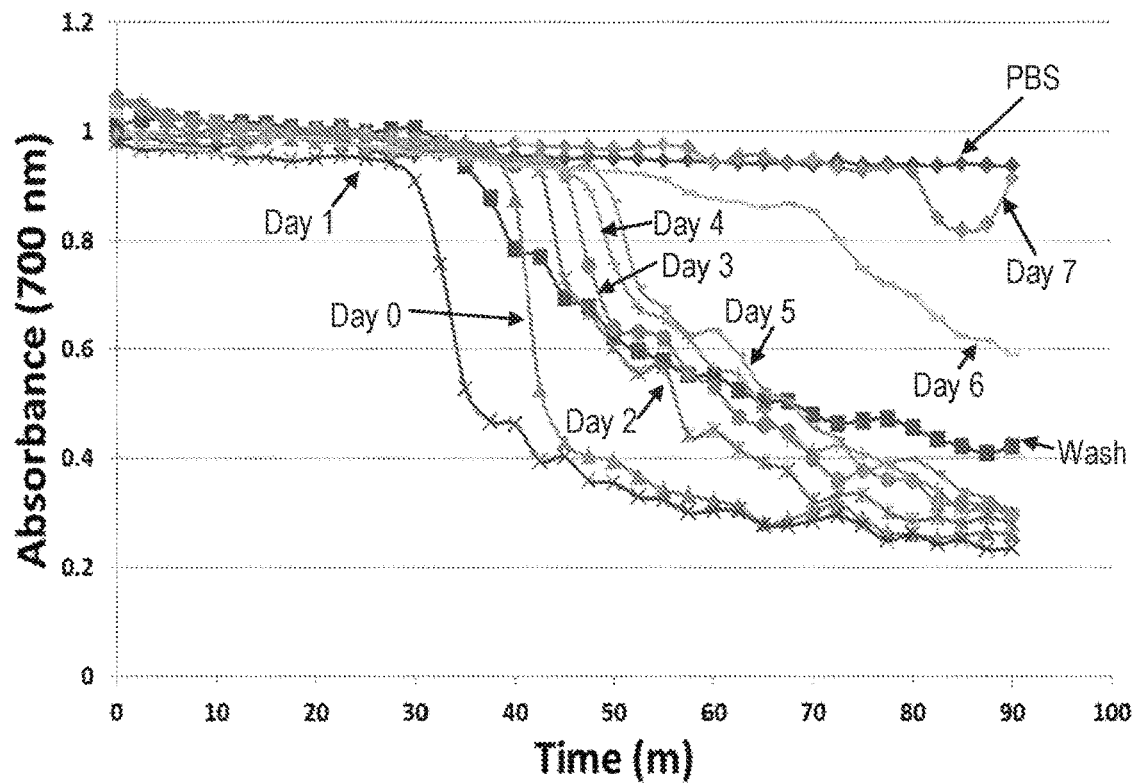
FIG. 7 shows biological activity of SPD protein that was released from PLGA 1A NPs during one week using bacterial aggregation assay. PBS: blue diamond, wash: red square, Day 0: green triangle, Day 1: purple X, Day 2: blue asterisk, Day 3: orange circle, Day 4: perpendicular bar, Day 5: brown line, Day 6: green line, Day 7: purple diamond.

To determine if the SPD released from nanoparticles is biologically active a bacterial aggregation assay was performed. The decreasing absorbance in FIG. 7 shows that SPD eluted from nanoparticles is biologically active, with activity slowly decreasing around day 2 and rapidly deteriorating by day 6. Though activity decreases over time, nanoparticles do release biologically active SPD protein for several days.

Example 7: In-Vitro Evaluation of PLGA NPs Toxicity

In order to investigate whether the NPs have toxic effect, cell viability was assessed using the MTT assay. 0.5 ml of A549 Lung cells were seeded in a 24 well plate at a density of 30,000 cells/well in DMEM growth medium and incubated at 37° C. and 5% $CO_2$ for 24 hours to promote cell attachment. Following incubation, the culture medium was removed, and the samples were washed twice with 0.5 ml phosphate buffered saline (PBS). PLGA 7A NPs with SP-D, as well as empty NPs for negative control, were dissolved in DMEM starvation medium (containing 1% L-glutamine, 1% penicillin-streptomycin, and 5% FBS) to final NPs concentration of 0.5 mg/ml or 1 mg/ml and incubated at 37° C. for 24 hr. Untreated A549 cells were used as the control. Following 24 hr incubation, a standard MTT assay was performed according to manufacturer's procedure. The samples were taken in triplicate.

Treatment with 0.5 mg/ml of PLGA 7A NPs showed around 80% cell viability and treatment with 1 mg/ml of PLGA 7A NPs showed cell viability values of about 70% (data not shown). The viability of the cells with empty NPs was about 80-90%. Although the concentration of NPs influences the cell viability, these high values indicate that the NPs are not toxic to the cells for both concentrations.

Example 8: Short Term Experiment—Acute Inflammatory Response

In order to determine whether NP administration induces an acute inflammatory response, C57Bl6 mice were treated with 10 μg per gram body weight of PLGA 7A NPs (2.0 mg/ml in PBS, n=4) or PBS for controls (n=4) given via tracheal injection. Six hours after injection, mice were subjected to bronchiolar lavage using 1 ml of PBS that was injected to the trachea. Bronchiolar Lavage Fluid (BALF) was collected, spun at 4000×g for 10 minutes and the remaining supernatant was tested for IL-6, a cytokine that drives acute inflammatory response thus can be an inflammation marker, using ELISA according to manufacture procedure.

Figure 8:
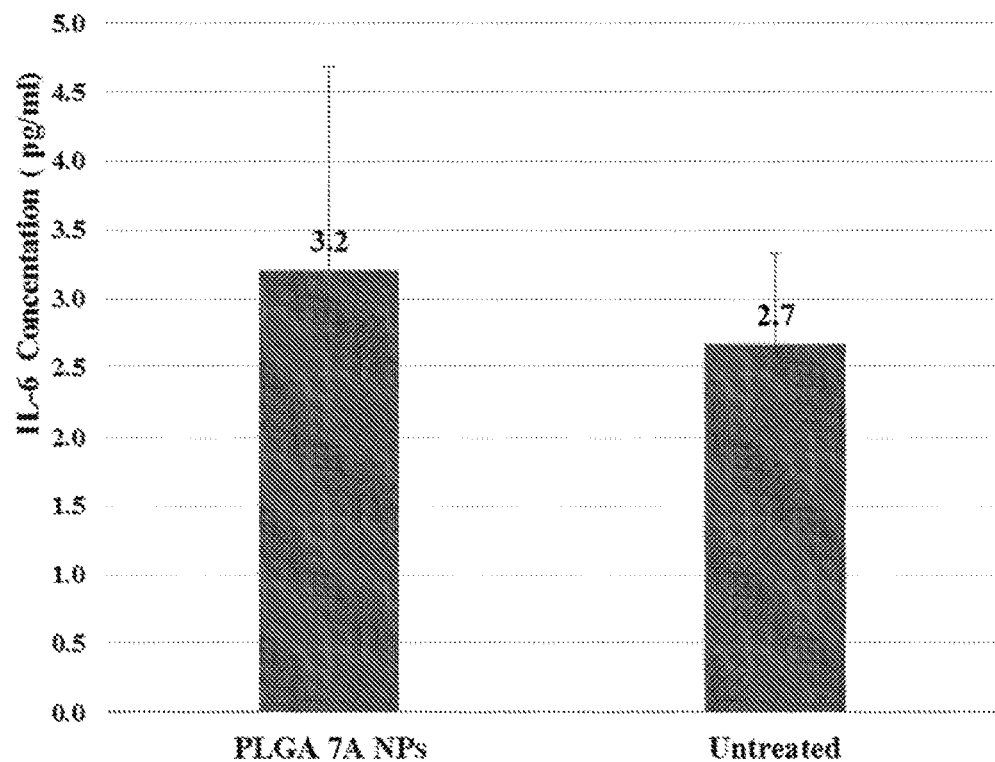
FIG. 8 shows short term toxicity test of C57bl/6 mice after intra-tracheal injection with PLGA 7A NPs at 10 µg particles per g body weight (left bar). Control group was injected with PBS (n=4, right bar). IL-6 concentration in Bronchiolar Lavage Fluid (BALF) was detected using ELISA.

The purpose of the In vivo toxicity test was to determine if treatment with empty PLGA NPs induces inflammatory response in mice before conducting in vivo experiments with SP-D loaded NPs. IL-6 is a pleiotropic, α-helical, 22-28 kDa phosphorylated and variably glycosylated cytokine that plays important roles in the acute phase reaction, inflammation, hematopoiesis, bone metabolism, and cancer progression. IL-6 drives the acute inflammatory response and it is almost solely responsible for fever. It is important in the transition from acute inflammation to either acquired immunity or chronic inflammatory disease (C. Garbers, H. M. Hermanns, F. Schaper, G. Müller-Newen, J. Gritzinger, S. Rose-John, J. Scheller, Plasticity and crosstalk of interleukin 6-type cytokines, Cytokine Growth Factor Rev. 23 (2012) 85-97). As can be seen from FIG. 8, IL-6 concentration in the lungs of mice treated with NPs was 3.2 pg/ml, similar to the level in untreated mice (2.7 pg/ml), indicating that no short term inflammation was observed as a result from PLGA 7A NPs treatment on mice by using tracheal injection.

Example 9: In Vivo SPD Release Experiment in Wild-Type Mice

In order to determine whether SP-D will be released from the NPs in the lungs, wild-type mice were injected intratracheally with SP-D loaded PLGA 7A NPs dissolved in PBS (2 mg/ml) at two different doses of 5 or 20 μg NPs per gram of body weight, to assess which dose will release the proper amount of SP-D. The control group was untreated mice. After Two days, 1 ml of Bronchiolar Lavage Fluid (BALF) was collected from the mice and centrifuge for 5 min at 10,000 RPM at temperature of 4° C. The resulting supernatant was assayed by human-SP-D ELISA, according to manufacture procedure, for SP-D concentration determination.

Figure 9:
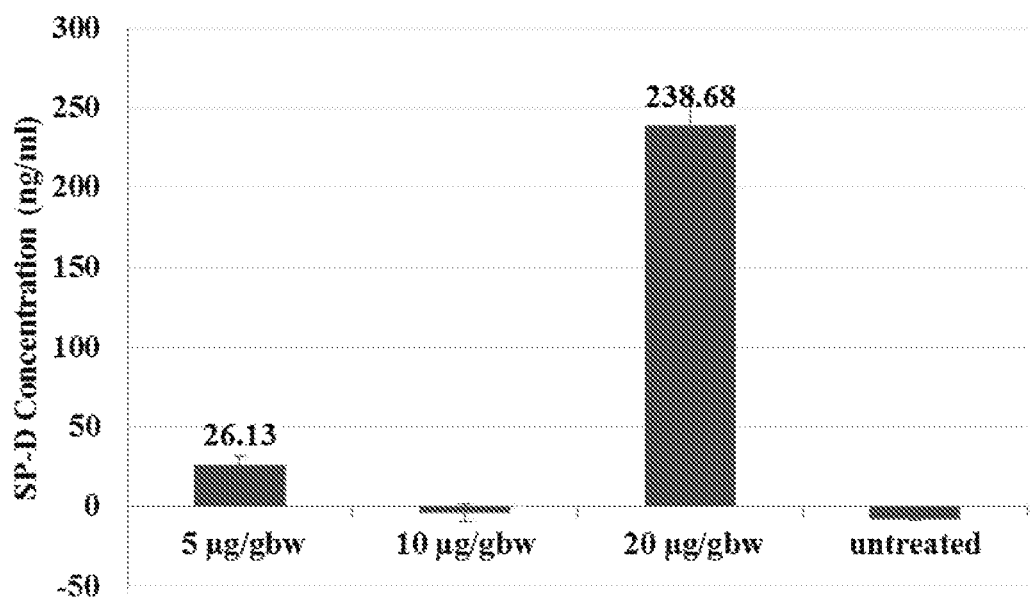
FIG. 9 shows SP-D concentration, measured by human SP-D ELISA, in bronchial lung lavage supernatant from wild-type mice after intra-tracheal injection of 5 (left bar), 10 (middle bar) or 20 (third bar from left) µg/g body weight (gbw) of PLGA 7A NPs with SP-D. Control group were untreated mice, (n=3) (right bar).

As can be observed in FIG. 9, for 1 ml BALF that was collected from the mice, negligible amount of SP-D was released from 5 and 10 µg/g body weight, while 239 ng of SP-D was released from 20 µg/g body weight. Since the ELISA is specific for human SP-D, as expected no SP-D was detected in the untreated mice control group. This finding emphasizes the fact that the SP-D that was found by using the ELISA is SP-D that was released from NPs only. The 239 ng SP-D that was released from 20 µg/g body weight of NPs fits to the preferred amount of SP-D needed in lungs of mice (100-300 ng), thus this dose was applied for further experiments with SP-D knock-out mice.

Example 10: In Vivo SPD Release Experiment in SPD Knock-Out Mice

After determination of the appropriate dose based on the wild-type mice experiment above, SP-D knock-out mice (disclosed in WO 00/23569) were treated with 20 g NPs per gram body weight of SP-D loaded PLGA 7A NPs by an intra-tracheal injection. The control groups were mice treated with empty PLGA 7A NPs or untreated. After 3 and 7 days, the amount of SP-D that was released from the NPs was determined using SP-D ELISA.

Figure 10:
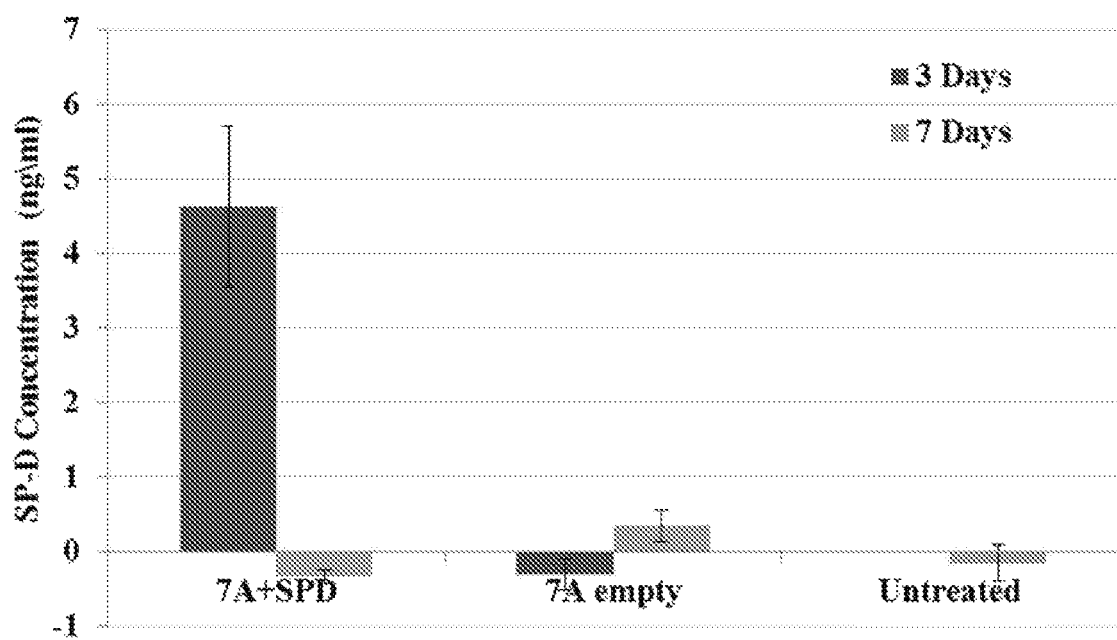
FIG. 10 shows SP-D concentration measured by human SP-D ELISA, in bronchial lung lavage supernatant from knock-out mice after intra-tracheal injection of PLGA 7A NPs with SP-D at 20 µg per gram body weight (left bars), or of empty PLGA 7A NPs (middle bars). Control group was untreated mice, (n=3) (right bar). Each group: left bar (dark)—measured after 3 days, right bar (light)—measured after 7 days.

As shown in FIG. 10, SP-D was released from NPs after 3 days but after 7 days there was no SP-D in the lungs. Moreover, the SP-D concentration extracted from the lungs fluids was lower than the concentration in the wild-type mice experiment described above. One explanation could be that for knock-out mice, more SP-D was consumed than in the wild type mice, which have SP-D naturally, and therefore the concentration was lower. It can be that changes in the experiment such as larger dose of NPs to be delivered will release appropriate amount of SP-D for one week.

Example 11: Decrease in Inflammation Following a Lung Injury Caused by Infection or Hyperoxia Lung injury is inflicted in wild-type or SPD knock-out mice by intratracheal or intranasal administration of bacteria, bacterial products such as LPS, virus or fungi; or by induction of hyperoxia for example by exposing the mice to >95% $O_2$ for 72 hrs. Injured mice are treated with an appropriate dose of PLGA 7A NPs complexed with human SPD by an intratracheal injection. The control group is injured mice treated with empty PLGA 7A NPs. After an appropriate time, for example when the control group exhibits significant signs of injury, lung lavage is evaluated for human SPD content by spinning 600 µl for 5 min at 10,000 RPM at 4° C. and assaying by SPD ELISA, and the extent of inflammation is assessed, for example by following neutrophilic alveolitis, indicating the presence of an inflammatory response in the alveoli.

To demonstrate treatment of emphysema and pulmonary infections, clearance of bacteria, virus and fungi from the lung is assessed in treated or un-treated SPD knock-out mice (for example as taught in WO 00/23569).

REFERENCES

Danhier et al, J. Controlled Release, 2012, 161(2):505-522
Ikegami et al. 2006, Am. J. Respir. Crit. Care Med. 173: 1342-1347
Kurnari et al, *Colloids and Surfaces B: Biointerfaces* (2010) 75:1-18)

What is claimed is:

1. A controlled release system comprising a nanoparticle or microparticle, wherein said nanoparticle or microparticle consists of surfactant protein D (SPD) as the active agent, a polymer carrier suitable for controlled release of the SPD, and optionally, polyvinyl alcohol.

2. The system according to claim 1, wherein said polymer carrier is selected from the group consisting of polylactic-co-glycolic acid (PLGA), polylactic acid (PLA), polyglycolic acid (PGA), chitosan, gelatin, polycaprolactone, and poly-alkyl-cyanoacrylates.

3. The system according to claim 2, wherein said polymer carrier is polylactic-co-glycolic acid (PLGA).

4. The system according to claim 3, wherein the ratio of lactic acid to glycolic acid in said PLGA is selected from the group consisting of 50:50, 65:35, 70:30, 75:25, 82:18 and 85:15.

5. The system according to claim 1, wherein said system is in the form of a nanoparticle.

6. The system according to claim 5, wherein the average radius of said nanoparticle is selected from the group consisting of between about 20 and about 300, between about 50 and about 150 nm, and about 100 nm.

7. The system according to claim 1 further comprising a pharmaceutically acceptable carrier.

8. The system according to claim 7, in the form of an aerosol.

9. A method for the treatment of a disease, disorder or condition selected from the group consisting of chronic obstructive lung disease (COPD), asthma, acute bronchitis, chronic bronchitis, bronchopulmonary dysplasia, emphysema, infant respiratory distress syndrome (IRDS), acute respiratory distress syndrome (ARDS), lung infections, persistent pulmonary hypertension, lung hypoplasia, cancer, cystic fibrosis, alveolar proteinosis, upper respiratory inflammation, congenital SP-B deficiency, respiratory syncytial virus (RSV), allergic rhinitis, influenza, and a disease, disorder or condition associated with a decreased level of SPD in a subject, comprising administering the system according to claim 1 to said subject.

10. A method for pulmonary delivery of SPD comprising administering to a subject in need thereof the system according to claim 1.

* * * * *